United States Patent [19]

Patel et al.

[11] Patent Number: 5,849,948
[45] Date of Patent: Dec. 15, 1998

US005849948A

[54] ALKYLATION OF AMINO ACIDS

[75] Inventors: Rajeshkumar Natwarlal Patel, Liverpool; Peter Michael Radley; Jonathan Richard Wiley, both of Chester; Robert Graham Tyson, Clywd, all of Great Britain

[73] Assignee: The Associated Octel Company Limited, London, England

[21] Appl. No.: 481,286

[22] PCT Filed: Nov. 2, 1994

[86] PCT No.: PCT/GB94/02397

§ 371 Date: Jan. 11, 1996

§ 102(e) Date: Jan. 11, 1996

[87] PCT Pub. No.: WO95/12570

PCT Pub. Date: May 11, 1995

[30] Foreign Application Priority Data

Nov. 3, 1993 [GB] United Kingdom .................. 9322648

[51] Int. Cl.⁶ .................................................. C07C 229/00
[52] U.S. Cl. ............................................................ 562/565
[58] Field of Search ............................................. 562/565

[56] References Cited

U.S. PATENT DOCUMENTS

| | | |
|---|---|---|
| 2,564,092 | 8/1951 | Bersworth . |
| 3,077,487 | 2/1963 | Ramsey et al. . |
| 3,158,636 | 11/1964 | Kezerian et al. . |
| 4,299,978 | 11/1981 | Nakayasu et al. . |
| 4,704,233 | 11/1987 | Hartman et al. . |
| 5,466,867 | 11/1995 | Lin et al. . |
| 5,550,285 | 8/1996 | Layman, Jr. et al. . |
| 5,554,791 | 9/1996 | Lin et al. . |
| 5,587,512 | 12/1996 | Lin .......................................... 562/565 |

FOREIGN PATENT DOCUMENTS

| | | |
|---|---|---|
| WO94/03572 | 2/1994 | WIPO . |
| WO96/01801 | 1/1996 | WIPO . |
| WO96/01802 | 1/1996 | WIPO . |
| WO96/01803 | 1/1996 | WIPO . |
| WO96/01804 | 1/1996 | WIPO . |

OTHER PUBLICATIONS

Greenstein, "Chemistry of Amino Acids," vol. 1, p. 3, 1961.
*Chemické Zvesti;* E. Dvorakova et al.; vol. 27, No. 11, pp. 313–317; ©Nov. 1, 1968.
*Inorganic Chemistry;* J. A. Neal et al.; vol. 7, No. 11, pp. 2405–2412; ©Nov. 1, 1958.
Chemical Abstract No. 207829f; T. Nishikori et al.; vol. 100, No. 25; ©Jun. 18, 1984.
"Stereospecific Ligands and Their Complexes. I. A. Cobalt (III) Complex of Ethylenediaminedisuccinic Acid"(J. A. Neal et al.; *Journal of Inorganic Chemistry;* vol. 7, No. 11, pp. 2405–2412; ©Nov. 1958).
"The Isolation of Some Complex Salts of New Complexanes and the Spectrophotometric Study of Their Structures" (Milan Kotouček et al.; *Acta Facultatis Pharmaceuticae;* TOM XXXII, 1978; pp. 1–30).
"Ethylenediamine Discussinates of Magnesium (II) and Calcium (II)" (I. B. Kovalyova et al.; *Journal of Inorganic Chemistry;* vol. 36, No. 3; pp. 1–7 ©1991).

*Primary Examiner*—Michael L. Shippen
*Attorney, Agent, or Firm*—Fay, Sharpe, Beall, Fagan, Minnich & McKee

[57] ABSTRACT

This invention provides improvements in certain processes for alkylating amino acids whereby yields based on amino acid are improved. More specifically, the invention provides a process for the preparation of amino acid derivatives in free acid or salt form, in which the nitrogen atoms of two or more amino acid molecules are linked by a hydrocarbyl or substituted hydrocarbyl group, which comprises reacting, in an aqueous medium at a pH in the range 7—14, a compound of the formula X—A—Y where X and Y are halo atoms which may be the same or different and A is a hydrocarbyl or substituted hydrocarbyl group, in which X and Y are attached to aliphatic or cycloaliphatic carbon atoms, with an amino acid (or salt thereof), wherein the reaction is carried out in the presence of dissolved cations of an alkaline earth metal or of a transition metal and/or wherein the unreacted amino acid is recovered and recycled.

1 Claim, No Drawings

ALKYLATION OF AMINO ACIDS

This invention relates to a process for alkylation of amino acids, and particularly though not exclusively a process for preparing (S,S)-ethylenediaminedisuccinic acid or a salt thereof.

Certain compounds having amino acid moieties linked by a group joining their nitrogen atoms have a variety of uses mainly based on their metal chelating properties e.g. as corrosion inhibitors, and in detergents, photographic developing solutions, rubber and resin formulations and metal treatments. One particular example is ethylenediaminedisuccinic acid which has two chiral centres, the S,S-enantiomer being preferred because of its biodegradability and its better chelating properties. It can be manufactured by a variety of different routes, e.g. the reaction of NaOH with L-aspartic acid and dibromoethane c.f. Neal, J. A. and Rose, N. J., Inorganic Chemistry, Vol. 7, No. 11, November 1968, pages 2405–2412, particularly page 2406, but whichever route is chosen it is usually difficult to obtain economic yields and a high purity product.

We have now found that the overall yield in alkylation reactions of this general type can be improved by the presence of certain metal ions. While we do not wish to be bound by any theory, it is likely that the amino acid starting material, the final product or both forms a complex with the metal ion which facilitates the desired reaction. The amino acid is relatively expensive but any which is unreacted can normally be recycled. Thus from the point of view of economic operation, reduction of by-product formation is highly significant.

More generally stated, one aspect of the invention provides a process for the preparation of amino acid derivatives in free acid or salt form, in which the nitrogen atoms of two or more amino acid molecules are linked by a hydrocarbyl or substituted hydrocarbyl group, which comprises reacting, in an aqueous medium at a pH in the range 7–14 and preferably in aqueous alkali, a compound of the formula X—A—Y where X and Y are halo atoms which may be the same or different and A is a hydrocarbyl or substituted hydrocarbyl group in which X and Y are attached to aliphatic or cycloaliphatic carbon atoms, with an amino acid (or salt thereof), wherein the reaction is carried out in the presence of dissolved cations of an alkaline earth metal or of a transition metal.

In the simplest cases A will have the formula —$C_nH_{2n}$— where n can be from 1 to 20, particularly 1 to 5, more especially 2, 3 or 4. Preferably it will be straight-chained i.e. —$(CH_2)_n$— but branched chain compounds can be used (e.g. compounds with alkyl substituents on the chain), as also can compounds with aryl groups such as phenyl (provided that X and Y are attached to an aliphatic or cycloaliphatic carbon atom) and cycloalkyl groups such as cyclohexyl in the main chain or in a side chain (as a monovalent, divalent or polyvalent group). A can also be divalent cycloalkyl without a —$(CH_2)_n$— chain. Cyclohexyl groups used with or without a —$(CH_2)_n$— chain can be 1,2-cyclohexyl, 1,3-cyclohexyl or 1,4-cyclohexyl, for example. Possible non-hydrocarbyl substituents include ether and thioether linkages, and hydroxy groups; they can be in a main chain or a side chain. Further halo atoms can also be present particularly if more than two amino acid molecules are to be linked. The substituents should basically not be groups which encourage unwanted side reactions. Olefinic unsaturation may also be present.

The term halo embraces chloro, bromo and iodo; in practice iodo compounds are undesirable for cost reasons. Bromo is preferred and chloro less preferred; one bromo atom and one chloro atom is another satisfactory possibility. The preferred X—A—Y compounds are dibromoethane and dichloroethane.

The amino acids will normally be one of the 26 or so naturally occurring amino acids listed in standard textbooks (except cysteine because of its —SH group which would undergo unwanted side reactions) viz. glycine, alanine, valine, leucine, norleucine, phenylalanine, tyrosine, serine, cystine, threonine, methionine, di-iodotyrosine, thyroxine, dibromotyrosine, tryptophan, proline and hydroxyproline (which are all "neutral"), aspartic acid, glutamic acid and β-hydroxyglutamic acid (which are all "acidic") and ornithine, arginine, lysine and histidine (which are all "basic" and less preferred for the reasons stated below). All these acids have an α-amino group but other amino acids e.g. phenylglycine or amino acids having a β-amino group such as β-alanine can be used. The preferred amino acids are those with two carboxyl groups and one amino group (preferably the "acidic" amino acids listed above). Aspartic and glutamic acid are the most preferred of the three. The "basic" amino acids have more potential for unwanted side reactions and are currently less preferred than the "neutral" amino acids. The presence of e.g. aryl groups is not significant; for example phenylalanine reacts satisfactorily. In the case of synthetic amino acids substituted hydrocarbyl groups e.g. of the various types outlined above may be present. Specific optical isomers, particularly the L-form, are desirable because they increase biodegradability and in some cases, may also improve the chelating effect.

The metal ion is desirably a divalent ion but ions of higher valencies can be used. The preferred ions are those of the alkaline-earth metals (Groups II/IIa) with Ca and Mg being preferred. Other preferred metals are transition metals, particularly Group IIb metals such as Zn and other metals of the first transition row (Sc, Ti, V, Cr, Mn, Fe, Co, Ni, Cu, Zn). It is important however to select metals which do not precipitate out, e.g. as oxides or hydroxides, under the reaction conditions (normally an alkaline pH).

The metal ion will normally be provided by a water-soluble metal salt although a water-soluble oxide or hydroxide may be used to raise the pH. $Ca(OH)_2$ can for example be used for this purpose (though its solubility is limited). Examples of salts include the divalent metal salts $CaCl_2$, $CaBr_2$, $MgCl_2$, and $ZnCl_2$. The reaction proceeds at a pH in the range 7–14, generally in the range 8–13 and preferably in the range 9–12. The pH may be maintained with alkali (i.e. a base), typically aq. NaOH solution, though a wide variety of water-soluble inorganic and organic bases may be used. It is desirable to add alkali during the reaction such that the pH remains substantially constant.

The reaction medium is normally wholly aqueous but the presence of other solvents such as ethanol is not excluded. In some circumstances, alkali (base) may be provided wholly or in part by other components of the reaction medium, particularly when the amino acid starting material is in salt form and/or when the metal cation is provided by a basic compound.

The amounts of metal salt included in the reaction mixture may generally range from 0.2 to 2.0 moles, preferably 0.2 to 1.5 moles, especially 0.3 to 1.0 moles, of cation per mole of amino acid.

The remaining parameters for the reaction are generally:

|  | General Range | Preferred Range |
|---|---|---|
| Amino acid:dihaloalkane mole ratio | 1:1 to 6:1 | 1.5:1 to 5:1 |
| Reaction Temperature | 70–120° C. | 85–100° C. |
| Reaction Period | 1–48 hours | 1–12 hours |
| pH | 7–14, e.g. 8–13 | 9–12 |

Particularly when using the more volatile dihaloalkanes, the reaction is desirably carried out under pressure e.g. 1–12 bar gauge, preferably 1–6 bar gauge.

The alkylated product is generally less soluble than the starting amino acid such that the reaction mixture can be diluted to a level at which remaining amino acid is soluble, followed by acidification and selective crystallisation of the desired product.

In the specific case of (S,S)-ethylenediaminedisuccinic acid prepared from L-aspartic acid and 1,2-dibromoethane, the reaction mixture is preferably held at boiling point for about 1 hour to reduce the level of unreacted 1,2-dibromoethane, diluted with water, acidified with an acid such as hydrochloric acid to a pH of from 2–5, preferably 2–3, and cooled to below about 50° C. to crystallise out the product acid. The crystalline product is separated from the mother liquor, and redissolved to make metal salts if desired. The mother liquor containing unreacted L-aspartic acid, inorganic and organic salt by-products, can be treated, e.g. by neutralisation and ion exchange, pervaporation, evaporation or nanofiltration, to separate out the inorganic and organic salt by-products, following which the mother liquor can be re-acidified and crystallised to recover the unreacted L-aspartic acid for recycle to the initial reactor. Recycle of the L-aspartic acid significantly improves the overall yield to the desired alkylated products.

The process of this invention is illustrated by the following Examples. In the Examples conversion means the weight of amino acid reacted (to form any product) divided by the weight of amino acid present initially ×100% and selectivity means the weight of amino acid reacted to form the desired product divided by the total amount of amino acid reacted ×100%. Yield means the weight of desired product produced divided by the weight which could theoretically be produced from the amino acid charged ×100%. DBE means 1,2-dibromoethane, (S,S)-EDDS means (S,S)-ethylenediaminedisuccinic acid, i.e. a compound of formula:

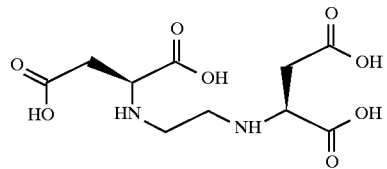

Example 1 is a comparative Example similar to Example 2; these Examples illustrate the effect of calcium ion in a reaction system where the mole ratio of amino acid to dihaloalkane is 3.6:1 and calcium is added as calcium bromide. Example 3 is a comparative Example similar to Example 4; these Examples illustrate the effect of calcium ions where the said mole ratio is 2.5:1 and calcium is added as calcium hydroxide. Again Example 5 is a comparative Example similar to Example 6; these Examples illustrate the effect of calcium ions where the said mole ratio is 2.02:1 and calcium is added as calcium hydroxide. Examples 7 and 8 are further Examples using calcium chloride. Examples 9 and 10 respectively use zinc chloride and magnesium chloride under conditions similar to those of Example 5. Example 12 is a comparative Example similar to Example 11, both employing L-glutamic acid. Example 14 is a comparative Example similar to Example 13, both employing phenylalanine. Example 16 is a comparative Example similar to Example 15, both employing 1,3-dibromopropane. Examples 17–19 illustrate amino acid recovery and recycle techniques.

EXAMPLE 1

A reaction mixture containing 150.1 g L-Aspartic acid, 140.0 g of 50% aq. NaOH, and 210.9 g water at a pH of 10.2 at 25° C. together with 57.8 g of DBE was heated at 85° C. for 4 hours. During this time an additional 50.1 g of 50% aq. NaOH was added to maintain the pH. At the end of the reaction period the solution was heated to boiling point for 1 hour then cooled to room temperature and 1633 g of water added. The solution was acidified with 36% HCl to pH 3 maintaining the temperature below 50° C. The solid product was collected by filtration. The solid product was (S,S)-Ethylenediaminedisuccinic acid (51.5 g on 100% basis), representing a yield on L-Aspartic acid charged of 31.3%, no other isomers being detected in the product. In the mother liquors was 85.7 g unreacted L-Aspartic acid. The conversion of L-Aspartic acid was 42.9% and selectivity to (S,S)-EDDS was 72.8%.

EXAMPLE 2

To a reaction mixture containing a slurry of 150.2 g L-Aspartic acid in 213.9 g water was added slowly 50% aq. NaOH (140.4 g) to a pH of 10.3 followed by 113.0 g calcium bromide. The resulting solution was heated at 85° C. and 57.6 g DBE added. The reaction mixture was maintained at 85° C. for 4 hours during which time 49.6 g of 50% aq. NaOH was added to maintain the pH. At the end of the reaction period the solution was heated to boiling point for 1 hour then cooled to room temperature and 1650 g of water was added. The solution was acidified with 36% HCl to pH 3 maintaining the temperature below 50° C. The solid product was (S,S)-Ethylenediaminedisuccinic acid (66.2 g on 100% basis), representing a yield on L-Aspartic acid charged of 40.1%, no other isomer being detected in the product. There was 84.9 g unreacted L-Aspartic acid. The conversion of L-Aspartic acid was 43.5% and the selectivity was 92.3%.

EXAMPLE 3

A reaction mixture containing L-Aspartic acid (150.2 g), 50% aq. NaOH (140.3 g), water (212.3 g) and DBE (84.1 g) was heated at 85° C. for 6 hours, and during that time an additional amount of 50% NaOH (72.6 g) was added. At the end of the reaction period the solution was heated to boiling for 1 hour then cooled and 1630 g water added. The solution was acidified to pH 3 with 36% HCl and the crystallised (S,S)-EDDS was recovered by filtration (63.5 g contained), a yield on charged L-Aspartic acid of 38.5%. There was 58.2 g of unreacted L-Aspartic acid. The conversion of L-Aspartic acid was 61.3% and the selectivity was 62.9%.

EXAMPLE 4

A reaction mixture containing L-Aspartic acid (150.9 g), 50% aq. NaOH (89.3 g), DBE (85.7 g) and calcium hydroxide (41.8 g) in water (210.7 g) was heated at 95° C. for 6 hours whilst 72.0 g 50% NaOH was added. The reaction mixture was heated at 105° C. (boiling point) for a further 1 hour. The reaction mixture was cooled and 602.3 g of water was added. The mixture was acidified to pH 3 with 36% HCl below 50° C. The product (S,S)-EDDS was recovered by filtration, (86.3 g), no other stereoisomer being detected. This represents a yield on L-Aspartic acid charged of 52.1%. There was 62.8 g of unreacted L-Aspartic acid; hence conversion of L-Aspartic acid was 58.4% and selectivity 89.2%.

EXAMPLE 5

A reaction mixture containing 150.2 g of L-Aspartic acid, 140.3 g 50% NaOH, 207.9 g water and 104.9 g DBE was heated at 85° C. for 7 hours, and during this time an additional 90.5 g of 50% aq. NaOH was added. The reaction mixture was heated to boiling point (103° C.) for 1 hour and then cooled and 1630 g water added. The solution was acidified with 36% HCl to a pH of 3 below 50° C. and the product (S,S)-EDDS was filtered off. This was found to contain 62.7 g product, representing a yield on charged L-Aspartic acid of 38%. In the mother liquors were found 43.4 g unreacted L-Aspartic acid representing a conversion of 71.1% and a selectivity of 53.4%.

EXAMPLE 6

In a 1 litre reactor was charged 210.1 g water and 150.8 g L-Aspartic acid. 79.23 g 47% NaOH was added with cooling and stirring maintaining the temperature below 30° C. 51.6 g of calcium hydroxide was added giving a pH of 11.2 followed by 105.9 g DBE. The reactor was pressurised with nitrogen and warmed to 95° C. under a pressure of 4 barg. This temperature and pressure was maintained for 7 hours during which time 89.7 g of 47% NaOH was added to the reaction mixture so as to maintain the pH. Still maintaining a reactor pressure of 4 barg. the contents were heated to 105° C. for 1 hour. The reaction mixture was then cooled to room temperature and the pressure released. A portion of 431 g water was added. The mixture was acidified to pH 3 and product (S,S)-EDDS collected as before, 117.5 g was obtained representing a yield on L-Aspartic charged of 71%. There was 40.5 g of unreacted L-Aspartic acid and hence the conversion was 73.1% and selectivity 97%.

EXAMPLE 7

A mixture of 150.1 g L-Aspartic acid, 139.5 g 50% aq. NaOH, 210.5 g water, 62.8 g calcium chloride and 84.7 g DBE was heated to 95° C. whilst 72.4 g of 50% aq. NaOH was added over 6 hours. The reaction mixture was heated to 105° C. for 1 hour and then cooled and diluted with 1636 g of water. The resultant liquors were acidified to pH 2.7 using 36% HCl and cooled to below 50° C. The product (S,S)-EDDS was recovered by filtration. 68.6 g was obtained representing a yield on L-Aspartic acid charged of 41.6%. There was 78.5 g of unreacted L-Aspartic acid hence a conversion of 47.7% and a selectivity to product of 87.3%.

EXAMPLE 8

Example 7 was repeated using 150.3 g L-Aspartic acid, 175.3 g 47% aq. NaOH, 127.5 g of DBE and 62.9 g of calcium chloride in 210.8 g water. 108.3 g 47% NaOH was added during a period of 7.5 hours at 95° C. The reaction mixture was heated to 105° C. for 1 hour then cooled and 503.5 g water added. The reaction mixture was acidified to pH 3 using 36% HCl below 50° C. and product (S,S)-EDDS was recovered as before giving 112.2 g product representing a yield of 68% on charged L-Aspartic acid. There was 30.7 g unreacted L-Aspartic acid and hence conversion of L-Aspartic acid was 79.6% and the selectivity to product was 85.4%.

EXAMPLE 9

To a mixture of 150.6 g L-Aspartic acid, 220.0 g of 47% NaOH, 76.8 g zinc chloride and 210.2 g water was added 105.8 g DBE. The reaction mixture was heated to 95° C. and held for 7.5 hours whilst 72.4 g 47% aq. NaOH was added. The reaction mixture was heated to 105° C. for 1 hour and then cooled and diluted with 502 g water. The resultant liquors were acidified to pH 3 with 36% HCl and product collected after 1 hour stirring. The product cake contained 95.8 g (S,S)-EDDS, a yield on charged L-Aspartic acid of 57.9%. There was 54.1 g unreacted L-Aspartic acid and so the conversion of L-Aspartic acid was 64.1 and selectivity to product was 90.3%.

EXAMPLE 10

To a mixture of 150.6 g L-Aspartic acid, 254.8 g 47% aq., NaOH, and 115.5 magnesium chloride hexahydrate in 209.8 g water was added 107.0 g of DBE. The mixture was heated to 85° C. and held for 7 hours during which time 107.2 g of 47% NaOH was added. The reaction was heated to 105° C. for a further 1 hour then cooled and 499 g of water was added. Product (S,S)-EDDS was recovered as before giving 112.5 g product, a yield of 68.1% with 32.5 g L-Aspartic acid unreacted, a conversion of 78.4% and a selectivity of 86.8%.

EXAMPLE 11

100.0 g of L-Glutamic acid was slurried in 254.9 g water, 57.5 g 47% aq. NaOH was added keeping the temperature below 500° C. 25.2 g of calcium hydroxide was added followed by 63.9 g DBE. The mixture was heated to 95° C. and 147.6 g of 47% aq. NaOH added over 7.5 hours. The mixture was heated to 105° C. for 1 hour then cooled and 500 g water was added. The mixture was cooled to below 50° C. and acidified to pH 3 with 36% HCl. The product was identified by proton and carbon NMR as ethylenediamine-diglutaric acid in a yield of 46% on starting amino acid.

EXAMPLE 12

110.1 g of L-Glutamic acid in 111.1 g water was treated with 89.0 g 47% aq. NaOH and then 63.4 g DBE. The mixture was heated to 95° C. and 57.4 g 47% aq. NaOH was added during 7.5 hours. The mixture was heated to 105° C. for 1 hour then cooled and diluted with 500 g of water then acidified to pH 3. The solid was dried to constant weight (15 g), identified by NMR as ethylenediaminediglutaric acid, the yield on charged glutamic acid was 13.8%.

EXAMPLE 13

50.0 g of L-Phenylalanine, 24.9 g of 47% NaOH, 11.2 g calcium hydroxide were mixed in 71.2 g water. 29.3 g of DBE was added and the mixture heated to 95° C. 26.2 g of 47% NaOH was added during 7 hours, then the mixture was held at 105° C. for 1 hour. The reaction mixture was diluted with 200 g water and then acidified to pH 3. The white solid was filtered off and dried to constant weight. The product was found to be ethylenediamindi-3-phenyl-propionic acid (EDDP) in 51% yield on charged amino acid.

EXAMPLE 14

Example 13 was repeated using 50.0 g of Phenylalanine, 39.9 g of 47% aq. NaOH, 28.5 g of DBE in 61.9 g water.

25.9 g of 47% aq. NaOH was added during the reaction period. The reaction liquors were diluted with 200.1 g water and then acidified to pH 3. The resulting solid was dried to a constant weight. This material was found to contain 15.9 g EDDP, a yield of 29% on phenylalanine charged.

EXAMPLE 15

A slurry of 50.1 g L-Aspartic acid in 70.9 g water was treated with 32.8 g 47% aq. NaOH and 14.0 calcium hydroxide; 33.0 g 1,3-dibromopropane was added. The mixture was heated to 95° C. and held for 7 hours while 31.7 g 47% aq. NaOH was added then heated to 105° C. for 1 hour. The reaction mixture was diluted with 200 g water and acidified to pH 3. The resulting solid (8.9 g dry wt.) was L-Aspartic acid. The mother liquors were evaporated to dryness (154.5 g); this sticky solid was analysed by HPLC and NMR to indicate the presence of propylenediaminedisuccinic acid.

EXAMPLE 16

Example 15 was repeated with 50.0 g L-Aspartic acid, 50.1 g 47% NaOH and 39.5 g 1,3-dibromopropane in 66.2 g of water. The reaction mixture was heated at 95° C. and 33.0 g of 47% NaOH was added over 7 hours. The mixture was held at 105° C. for 1 hour, cooled and diluted with water as before and acidified to pH 3. No solid was precipitated. There was no evidence found for the desired product in the reaction liquors.

EXAMPLE 17

To a slurry of 149.5 g L-Aspartic acid in 213.3 g water was added 90.25 g 50% NaOH and 41.7 g calcium hydroxide. To this was added 106.5 g DBE. The reaction mixture was heated to 90° C. for 7.5 hours during which time 90.1 g of 50% (aq.) NaOH was added. The reaction mixture was then heated to 105° C. for 1 hour and then cooled; water (404.5 g) was added and then the solution was acidified to pH 3. The crystallised product was washed with water and found to be 108.1 g (S,S)-EDDS. The combined mother liquor and washes contained 38.9 g L-Aspartic acid, a conversion of 74% and selectivity of 89%. The combined liquors were neutralised with 23.7 g 50% NaOH and then passed through a nanofiltration membrane (AFC 30) to give a volumetric concentration factor of 5.3. The resulting retentate, 290 g, contained 32.1 g L-Aspartic acid in sodium salt form. The retentate was acidified with 36% HCl to pH 3 giving a crystalline solid, 15.3 g L-Aspartic acid. The yield of (S,S)-EDDS on L-Aspartic acid was 67%.

EXAMPLE 18

The procedure of Example 1 was followed using 150.2 g L-Aspartic acid, 211.4 g water, 140 g 50% NaOH and 57.6 g DBE. 50.5 g of 50% NaOH was added during the reaction. 48.4 g (S,S)-EDDS was isolated leaving 85.6 g L-Aspartic acid in the mother liquor, a conversion of 43.8 and selectivity of 70.4%. The mother liquor was further acidified to pH 2.6 and after stirring for 3 hours a further precipitate had formed. The precipitate was filtered off and found to be 24.1 g L-Aspartic acid, representing a yield of (S,S)-EDDS on L-Aspartic acid of 35%.

EXAMPLE 19

To a slurry of 291.9 g L-Aspartic acid, 422 g of water, and 280 g 50% aq. NaOH was added 115.6 g DBE. The mixture was heated to 85° C. and 100 g of 50% NaOH added over 4 hours. The mixture was warmed to boiling for 1 hour then cooled and acidified to pH 3. The product collected by filtration and washing with 200 g water was 92.4 g (S,S)-EDDS. 166.1 g L-Aspartic acid remained in the mother liquor and wash water representing a conversion of 43.1% and a yield at this point of 28.9%. The combined mother liquor and wash water were neutralised with 50% NaOH and the resulting solution evaporated at 80° C. under reduced pressure to 20% of original weight. The resulting liquor was then acidified with 36% HCl to pH 2.6 resulting in precipitation of 85.2 g of L-Aspartic acid which is recovered as a white crystalline mass with 43.6 g remaining in the mother liquor. The amount of L-Aspartic acid recovered is 85.2 g representing a yield of (S,S)-EDDS on L-Aspartic acid of 40.7%.

The recovered L-Aspartic acid was then reused together with 211.8 g of fresh L-Aspartic acid in a reaction as described above resulting in 101.4 g (S,S)-EDDS isolated. The mother liquor from the L-Aspartic crystallisation in the previous experiment was combined with the mother liquors from the (S,S)-EDDS crystallisation in this experiment and the combined liquors were neutralised, evaporated and acidified as before, 35.6 g of L-Aspartic acid being recovered. This procedure was repeated for 12 cycles producing a total weight of 1018.9 g (S,S)-EDDS and consuming 1452.5 g L-Aspartic acid. This represents an overall yield of 63.9%.

The invention further extends to the concept of recycling the amino acid to the process (whether or not the metal is present). Thus according to yet another aspect the invention provides a process for the preparation of amino acid derivatives in free acid or salt form, in which the nitrogen atoms of two or more amino acid molecules are linked by a hydrocarbyl or substituted hydrocarbyl group, which comprises reacting, in an aqueous medium at a pH in the range 7–14, and preferably in aqueous alkali, a compound of the formula X—A—Y where X and Y are halo atoms which may be the same or different and A is a hydrocarbyl or substituted hydrocarbyl group, in which X and Y are attached to aliphatic or cycloaliphatic carbon atoms, with an amino acid (or salt thereof), including the step of recovering unreacted amino acid and recycling it to the process. Preferred features are set out above and in the dependent claims.

We claim:

1. A process for the preparation of (S,S)-ethylenediaminedisuccinic acid, which comprises reacting a 1,2-dihaloethane with L-aspartic acid in aqueous alkali, and recovering the product (S,S)-ethylenediaminedisuccinic acid from the reaction mixture, wherein the reaction is carried out in the presence of a water-soluble salt of a Gp II/IIa or transition metal.

* * * * *